(12) United States Patent
Mir

(10) Patent No.: US 11,061,013 B2
(45) Date of Patent: Jul. 13, 2021

(54) SINGLE MOLECULE PROTEOMICS

(71) Applicant: Kalim Mir, Cambridge, MA (US)

(72) Inventor: Kalim Mir, Cambridge, MA (US)

( * ) Notice: Subject to any disclaimer, the term of this patent is extended or adjusted under 35 U.S.C. 154(b) by 0 days.

(21) Appl. No.: 16/011,337

(22) Filed: Jun. 18, 2018

(65) Prior Publication Data

US 2018/0364213 A1 Dec. 20, 2018

Related U.S. Application Data

(63) Continuation of application No. 15/328,743, filed as application No. PCT/US2015/042127 on Jul. 24, 2015, now abandoned.

(60) Provisional application No. 62/029,376, filed on Jul. 25, 2014.

(51) Int. Cl.
*G01N 21/64* (2006.01)
*G01N 33/58* (2006.01)
*G01N 33/68* (2006.01)
*G01N 33/487* (2006.01)
*G16B 30/00* (2019.01)
*G16B 20/00* (2019.01)

(52) U.S. Cl.
CPC ... *G01N 33/48721* (2013.01); *G01N 21/6486* (2013.01); *G01N 33/58* (2013.01); *G01N 33/582* (2013.01); *G01N 33/6803* (2013.01); *G01N 33/6842* (2013.01); *G16B 20/00* (2019.02); *G16B 30/00* (2019.02); *G01N 2458/00* (2013.01)

(58) Field of Classification Search
CPC ............ G01N 33/48721; G01N 33/58; G01N 33/582; G01N 33/68; G01N 33/6803; G01N 33/6818; G01N 33/6842; G01N 33/583; G01N 2458/00; G01N 2458/10; G01N 21/6486

See application file for complete search history.

(56) References Cited

U.S. PATENT DOCUMENTS

| 7,744,816 B2 * | 6/2010 | Su | ...................... G01N 33/6803 |
| | | | 422/68.1 |
| 8,278,055 B2 * | 10/2012 | Su | ..................... G01N 33/48721 |
| | | | 435/7.1 |
| 2005/0148100 A1 * | 7/2005 | Su | ........................ C12Q 1/6816 |
| | | | 436/523 |

FOREIGN PATENT DOCUMENTS

| WO | WO-0125794 A2 * | 4/2001 | ............ G01N 33/542 |
| WO | WO-2012121756 A1 * | 9/2012 | ............ C12Q 1/6869 |
| WO | WO-2014014347 A1 * | 1/2014 | ........ G01N 33/48721 |

OTHER PUBLICATIONS

Baker et al. ClpXP, an ATP-powered unfolding and protein-degradation machine. Biochimica et Biophysica Acta. 2012, vol. 1823, pp. 15-28. (Year: 2012).*

(Continued)

*Primary Examiner* — Jeffrey E. Russel
(74) *Attorney, Agent, or Firm* — Morgan, Lewis & Bockius LLP

(57) ABSTRACT

This disclosure comprises devices and methods for determining the identity of individual protein molecules in a complex mixture by unfolding the protein into a polypeptide, tagging selected residues on the polypeptide with selected oligonucleotide sequence tags that recognize selected residues on said polypeptide, and then detecting the oligonucleotide sequence tags.

16 Claims, 2 Drawing Sheets

(56) References Cited

OTHER PUBLICATIONS

Nivala et al. Unfoldase-mediated protein translocation through an alpha-hemolysin nanopore. Nature Biotechnology. Mar. 2013, vol. 31, No. 3, pp. 247-251. (Year: 2013).*
Notingher et al. Raman spectroscopy cell-based biosensors. Sensors. 2007, vol. 7, No. 8, pp. 1345-1358. (Year: 2007).*

* cited by examiner

EXPERIMENTAL METHODS

SINGLE MOLECULE PROTEOMICS

RELATED APPLICATION

This application claims priority under 35 U.S.C. § 119 to U.S. provisional patent application, U.S. Ser. No. 62/029,376, filed Jul. 25, 2014, entitled "SINGLE MOLECULE PROTEOMICS," the entire contents of which are incorporated herein by reference.

BACKGROUND OF DISCLOSURE

A number of methods are available for analyzing protein samples. This includes immunoassays, microarrays, 2-D gel electrophoresis and mass spectrometry. Recently, analysis of single protein molecules has been explored.

SUMMARY OF DISCLOSURE

Aspects of the disclosure relate to methods for identifying proteins, e.g., proteins present in a complex mixture. In some embodiments, the methods involve experimentally determining a distinct fingerprint for each individual protein based on the location of specific residues along the polypeptide length of the protein. In some embodiments, the protein is denatured/unfolded into a polypeptide form and the linear length of the polypeptide is determined and features along its length are analyzed. In one embodiment the linear length of the polypeptide is analyzed by stretching the polypeptide and determining the pattern or location of distinct residues along its length using an imaging or scanning method. The distinct residues can be determined by a number of means including labeling them with detectable labels that are specific to particular residues or that are conjugated to other molecules, e.g., antibodies, that are specific to particular residues. Alternatively, in some embodiments, the length of the polypeptide is analysed by passing it through a nanopore or nanogap and the pattern or location of distinct residues is determined by recording the length of time between signals. In some embodiments, an experimentally determined location of distinct residues in each individual polypeptide is then compared to a database comprising the location of distinct residues in each known or predicted protein. It is estimated that there are approximately 20,000 proteins in the human proteome as well as alternatively spliced isoforms, mutants, fusions, and versions modified by glycosylation, phosphorylation, methylation and acetylation, etc. In some embodiments, a match to the database indicates the identity of the unknown protein in the complex mixture under analysis. In some embodiments, methods disclosed herein are applied to complex protein mixtures from biological samples. In some embodiments the samples are of high complexity and dynamic range, e.g., the blood proteome and in some embodiments, such as single human cells or lower eukaryotes such as yeast the dynamic range is lower. In some embodiments, the aim is to access medium to low abundance proteins. Accordingly, some aspects of the disclosure involve the prior fractionation, enrichment and/or depletion of certain sub-sets of the protein population.

In some embodiments, methods provided herein comprise analyzing the linear length of a polymer to determine a pattern along a polymer (and optionally the length of the polymer). In some embodiments, the methods further comprise using the pattern along the polymer (and optionally the length) to determine or assign the identity of the polymer or candidates for the identity of the polymer.

In other embodiments, methods provided herein comprise analyzing the linear length of a polymer to determine the location, distance between and/or order of specific residues and optionally the length of the polymer. In some embodiments, the methods further comprise using the order, relative distance or coordinates of the specific residues on the polymer (and optionally length) to determine or assign the identity of the polymer.

In other embodiments, methods provided herein comprise analyzing the linear length of a polymer to determine the location, distance between and/or order of specific residues and optionally the length of the polymer. In some embodiments, the methods further comprise using the order, relative distance or coordinates of the specific residues on the polymer (and optionally length) to determine or assign the identity of the polymer or candidates for the identity of the polymer. In some embodiments, only a subset of residues are analysed.

In other embodiments, methods provided herein comprises unfolding the protein into a polypeptide. In some embodiments, the methods further comprise analyzing the linear length of the polypeptide to determine the location, distance between and/or order of specific residues and optionally the length of the polypeptide. In some embodiments, the methods further comprise using the length and/or order, relative distance or coordinates of the specific residues on the polypeptide (and optionally the length of the polypeptide) to determine or assign the identity of the protein or candidates for the identity of the protein.

In other embodiments, methods are provided herein that comprise unfolding a protein into a polypeptide, analyzing the linear length of the polypeptide to determine the location, distance between and/or order of specific residues and optionally the length of the polypeptide, and using the length and/or order, relative distance or coordinates of the specific residues on the polypeptide (and optionally the length of the polypeptide) to determine or assign the identity of the protein or candidates for the identity of the protein. In some embodiments, only a subset of residues are analysed.

In other embodiments, methods are provided herein that comprise unfolding a protein into a polypeptide, and analyzing the linear length of the polypeptide to determine a pattern of a physicochemical property, e.g., hydrophobicity. In other embodiments, the methods further comprise using the length and/or the pattern of a physicochemical property to determine or assign the identity of the protein or candidates for the identity of the protein.

In other embodiments, methods are provided herein that comprise unfolding a protein into a polypeptide and labeling residues along the polypeptide. In some embodiments, the residues are labeled prior to unfolding. In some embodiments, the residues are labeled following unfolding. In some embodiments, such methods further comprise analyzing the linear length of the polypeptide to determine a distinct pattern of labels and optionally the length of the polypeptide. In some embodiments, such methods further comprise using the distinct pattern of labels on the polypeptide (and optionally the length of the polypeptide) to determine or assign the identity of the protein or candidates for the identity of the protein.

In some embodiments, methods provided herein comprise unfolding a protein into a polypeptide, labeling residues along the polypeptide, analyzing the linear length of the polypeptide to determine the location, distance between and/or order of the labeled residues and optionally the length of the polypeptide, and using the length and/or order, relative distance or coordinates of the labeled residues on the polypeptide (and optionally) the length of the polypeptide to determine or assign the identity of the polypeptide or candidates for the identity of the protein.

In some embodiments, methods provided herein comprise depleting high abundance proteins and/or enriching medium and/or low abundance proteins. In some embodiments, such methods further comprise analyzing the remaining polypeptides at the single molecule level. In some embodiments, such methods further comprise comparing a pattern/data from each individual polypeptide to a protein database. In some embodiments, the comparison yields the identity of the protein or candidates for the identity of the protein.

In some embodiments, the methods further comprise enriching specific proteins. In some embodiments, the methods comprise analyzing the enriched polypeptides at the single molecule level. In some embodiments, the methods further comprise comparing a pattern/data from each individual polypeptide to a protein database. In some embodiments, the comparison yields the identity of the protein or candidates for the identity of the protein.

In some embodiments, an experimentally derived pattern of labels or data for label location distance between and/or order of, is compared to one or more in silico generated patterns of known proteins or to the sequence of known proteins. In some embodiments the apparent length of the polypeptide is also used in making a determination. In other cases (where for example the protein may be truncated) the length is not used. Other features of the protein may be determined to facilitate matching to the database, for example the net charge on the polypeptide may be determined.

Optionally more than one type of residue is labeled and, in some cases, each different type of residue is labeled with a distinct tag or label. In some embodiments, the tag is a DNA sequence. In some embodiments, the DNA tag acts as a docking site/handle for DNA PAINT (Points Accumulation for Imaging in Nanoscale Topography) [Jungmann et al, Nano Lett. 2010 Nov. 10; 10(11):4756-61.] In some embodiments, recording of the binding of DNA PAINTS enables a super-resolution picture to be constructed.

In some embodiments, analyzing the linear length comprises translocating the polypeptide through a detection station (e.g., nanopore, nanogap) and making real time recordings of physical phenomena as each residue along the polypeptide comes into the proximity of the station. In some embodiments, the physical phenomena is an optical signal. In other embodiments the physical phenomena is an electrical signal. In some embodiments, both optical and electrical signals are analysed. In some embodiments, translocating of the polypeptide is controlled by electrophoretic forces, hydrodynamic forces, pressure driven flow or physical pulling.

In some embodiments the polypeptide passes through a nanopore and a change in ion flux is detected according to the label that passes the pore, as illustrated in FIG. 2A. In some embodiments, the polypeptide passes through a nanogap electrode system. In some embodiments, the nanogap electrode system can produce a tunneling current and such tunneling can be perturbed to a different degree by labels or tags on the polypeptide, as illustrated in FIG. 2B. In some embodiments the nanogap is associated with an electrical field, capacitance, permittivity, etc. and a measurable quantity related to the electrical field, permittivity, capacitance etc. is perturbed to different degree by labels or tags.

In some embodiments, the polypeptide passes through an evanescent wave or a waveguide (e.g., a zero-mode waveguide). In some embodiments, the polypeptide passes a fluorophore, whose fluorescence emission is sensitive to its physical environment and different labels on the polypeptide elicit different fluorescent responses such as attenuation of the signal. In some embodiments, the label on the residue is a quencher and quenches the signal of the label at the detection station. In some embodiments the label on the residue is a FRET acceptor and the label on the detection station is a FRET Donor or vice versa. In some embodiments, the label is polylabeled to elicit an enhanced response. In some embodiments the station comprises features which enhance the signal of the label; such features include metallic structures at which are known to enhance fluorescent or Raman signals. In some embodiments the proximal location to nanostructures is tuned.

In some embodiments, analyzing the linear length comprises passing the polypeptide through a nanochannel or nanoslit and imaging the linear length as it passes through. In some embodiments, analyzing the linear length comprises attenuating the translocation of the polynucleotide through a nanochannel or nanoslit so that one or more images can be taken. In some embodiments the velocity of translocation of the polypeptide is matched to the speed of read-out of the CCD chip (operated in Time-Delay Integration (TDI) mode) so that polypeptide can be imaged whilst in motion; this can lead to faster data acquisition. An array of polypeptides can be stretched in an array of nanochannels. In some embodiments, the polypeptide is placed on a surface in a non-globular form and preferably the polypeptide is stretched on the surface. An array of polypeptides can be imaged using a CCD camera or a 2-D array CMOS detector.

Various methods can be used to give a resolution beyond the diffraction limit of light. Alternatively the surface can be scanned by methods such as scanning probe microscopies (as illustrated in FIG. 2C) or laser scanning microscopies. In one embodiment, an optical signal is detected as the labeled polypeptide passes through a nanopore or a nanogap.

In some embodiments, specific chemical moieties such as cholesterol are attached to the polypeptides. In some embodiments the residues that are attached comprise a polymer. Such a polymers may wrap around the polypeptide to homogenize the backbone charge. Other polymers can be grafted onto one or both ends of the polypeptide. The polypeptide can then be manipulated according to the properties of the polymer.

In some embodiments, an identity is assigned to each polypeptide according to the pattern of labels detected or data derived from the polypeptide. Preferably the experimentally derived pattern is compared to an in silico generated pattern or the experimentally derived coordinates are compared to the coordinates in the sequence of residues of proteins in a database by using parallel computing. Such parallel computing includes use of cloud-based computing and Graphics processing unit (GPU), which have a large number of processing cores.

In some embodiments, as an alternative to a comparison of predicted patterns and data, experimental data is obtained of purified proteins, a database is created and then the test polypeptide is compared to the previously acquired experimental data.

In some embodiments the protein population is handled collectively until the detection step, whereupon each protein in the population is handled individually and/or detected individually.

The abundance of each protein in the sample is determined by enumerating the number of occurrences of a match of individual polypeptides to each protein in a database.

In some embodiments, a whole process from sample collection to report of results can involve one or more of the following steps:

1) Collecting or acquiring a sample cells, tissues or organisms; in the case of blood, preferably isolating plasma 2) Extracting or isolating proteins from the sample 3) Depleting high abundance proteins/Enriching lower abundance proteins 4) Labeling the proteins at one type of residue with a distinct label or tag 5) Optionally labeling the proteins at another type of residue using a second distinct label or tag, which is distinguishable from the first label or tag (and label further residues with distinct labels, if necessary)

6) Rendering the proteins into a substantially unfolded polypeptide form (this step can optionally occur before step 4)

7) Optionally contacting the polypeptide with moieties (including polymers such as spermine or polynucleotides) that facilitate physical manipulation of the polypeptide 8) Handling each polypeptide individually 9) Detecting the order, location or distance between labels or specific physico-chemical features on the polypeptide or the distinct pattern of labels or specific physicochemical features on the polypeptide; optionally filtering data using hardware/digital signal processing 10) Analyzing the experimentally derived pattern/data and assigning an identity to the polypeptide under analysis wherein the analysis may comprise comparison to a database of proteins and is preferably conducted by parallel computing 11) Analysis is optionally done on the fly 12) Optionally providing a list of proteins present in the sample and optionally their abundance in the sample One of the simplest fingerprint parameter of a protein is whether it binds to a specific probe or not, and this can be achieved using the disclosure with medium to low abundance proteins by applying prior fractionation, enrichment and/or depletion. In some embodiments various means of detecting proteins can be applied at the single molecule level, including binding to an antibody array.

Therefore, in some embodiments, the disclosure comprises:

(i) depleting high abundance proteins and/or enriching medium and/or low abundance proteins or enriching specific proteins or purifying specific proteins; and (ii) analyzing the enriched/purified/non-depleted proteins by single molecule detection In some embodiments, the ultimate fingerprint of the proteins is the entire sequence of each polypeptide and this can be achieved using the disclosure with medium to low abundance proteins by applying prior fractionation, enrichment and/or depletion.

Therefore, in some embodiments, the disclosure comprises.

(i) depleting high abundance proteins and/or enriching medium and/or low abundance proteins or enriching specific proteins or purifying specific proteins;

(ii) analyzing the enriched/purified/non-depleted proteins, polypeptides at the single molecule level;

(iii) detecting each individual residue or pairs of individual residues or individual oligopeptides along the length of the polypeptide; and (iv) processing the collected data to provide the complete or partial sequence of the target polypeptide(s). In some embodiments, a motor protein/unfoldase/chaperonins are applied to the polypeptide(s) being sequenced. In some embodiments, in which pairs of amino acids or oligopeptides are individually detected, the identity of the signals are decoded with reference to a look up table and a sliding window of analysis is optionally applied. This analysis can include for example a sliding window comprising a first unit as amino acids 1-8, 2-9, 2-10, 4-11 etc. Eight amino acids is approximately the length of resolvability of the MspA nanopore which has a narrow constriction.

In some embodiments the proteins comprise the proteome of body fluids such as blood or enriched/depleted versions thereof; plasma is preferred over whole blood or serum due to lower ex vivo protein degradation. The proteome of other body components or waste can also be examined. In some embodiments the proteins comprise the protein contents of a single cell. In some embodiments the proteins comprise secreted proteins from multiple cells or a single cell. In some embodiments proteins comprise proteins that have recently been transported across a membrane and as a consequence of the transporting process are rendered as unfolded polypeptides.

DETAILED DESCRIPTION OF DISCLOSURE

Figure 1:
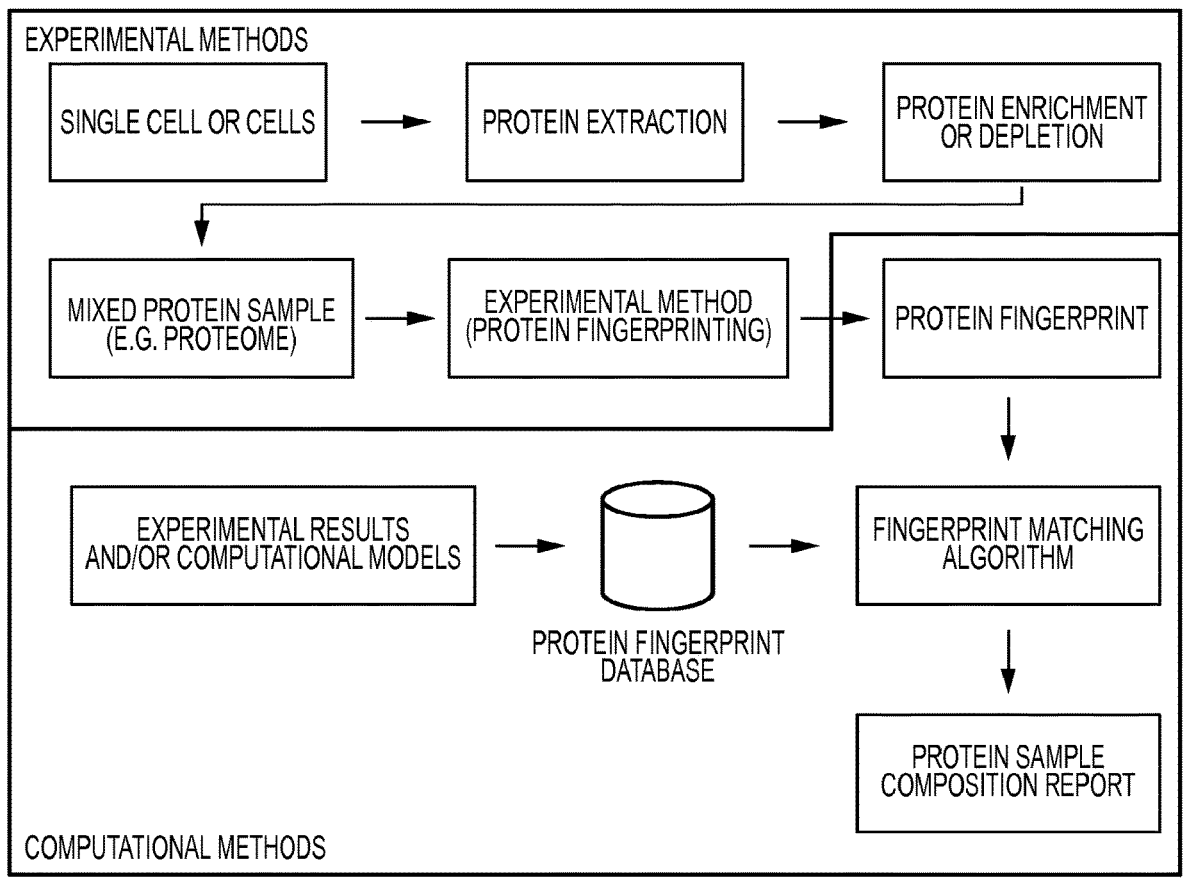
FIG. 1 provides a non-limiting illustration of a workflow for protein fingerprinting.
Figure 2A:
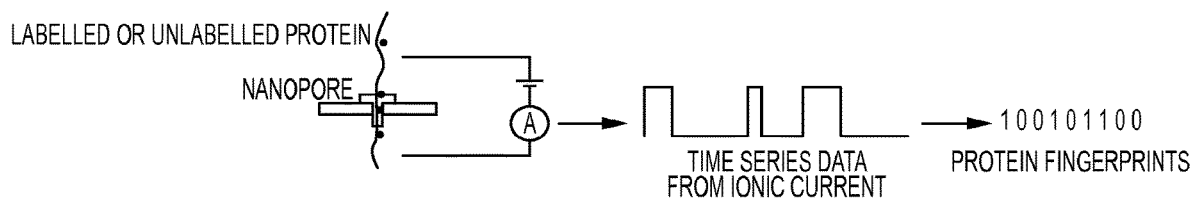
FIGS. 2A-2C provide non-limiting illustrations of labeled or unlabeled protein fingerprinting.
Figure 2B:
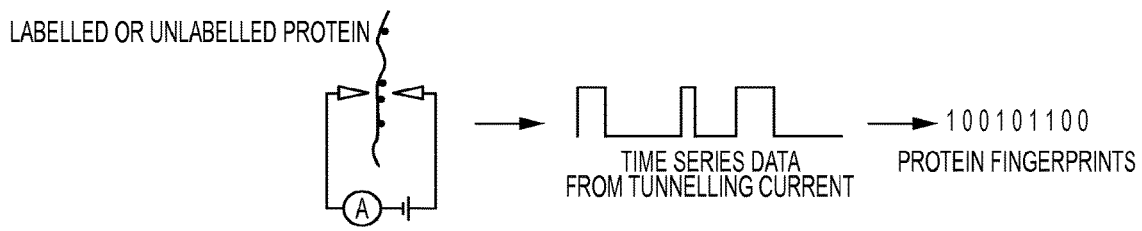
Figure 2C:
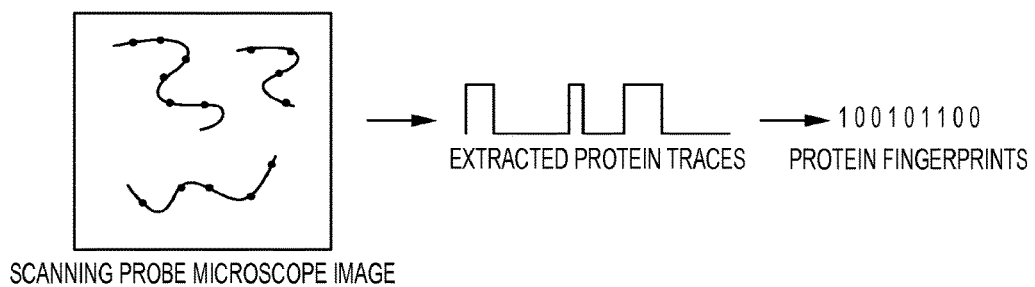

Aspects of the disclosure relate unfolding of the protein and disposing it in a non-globular substantially linear manner so that its length and residues along its length can be examined. Other aspects of the disclosure relate labeling of the residues and/or the labeling of a probe, which is optional depending on the mode of the disclosure being practiced. Other aspects of the disclosure relate to detection of features along the linear length of the polypeptide. Other aspects of the disclosure relate to identifying the protein by comparison of the experimentally derived details or patterns to a database of the expected details or patterns of known proteins. These and other aspects of the disclosure are described further below. In some embodiments, methods are provided herein that enable proteins to be analysed directly from a complex mixture without the need for prior separation or purification.

Extracting Proteins

Cell-free Proteins can be extracted form body fluids using standard techniques. Blood can be spun down, and the Plasma fraction is collected and the protein fraction therein is precipitated and collected. Proteins can be extracted from cells using detergents such CellLytic M (Sigma-Aldrich).

Single Cells

Single cells can be processed (including cultured) sorted and trapped in microfluidic devices. The trapped cells can lysed on-chip and the contents of each individual can be collected and prepared separately, much as has been done for RNA and RNA in Cl system by Fluidigm.

Depletion, Normalization and Enrichment

The dynamic range of proteins in biological samples can extend over nine orders of magnitude. Certain high abundance proteins are at such high levels that the low abundance proteins are very difficult to detect and even medium abundance proteins are difficult to quantify. Therefore in order to detect the low and medium abundance proteins specific measures provided by this disclosure need to be taken.

Fractionation

The protein population can be fractionated prior to analysis. This fractionation can be based on affinity purification of different classes of proteins, for example immunoglobulins can be isolated by binding to their Fc portions.

One important embodiment of this disclosure is fractionation based on abundance and/or electrophoretic properties and/or other physicochemical properties, e.g., those detected by liquid chromatography, mass spectrometry etc. In one specific embodiment, the population of proteins is fractionated by using isoelectric focusing, e.g., in 1-D or 2-D gel electrophoresis or via chromatography (iso-focusing chromatography). Then the bands pertaining to the high abundance proteins (bands with high intensity after staining) are cut out and removed. The remaining proteins in the gel can then be eluted out and analyzed by the methods of this disclosure. Taking this to the extreme, all visible bands are cut out, and elution is carried out on the remaining parts of the gel, collecting proteins that were not visible. Of course low abundance proteins that co-locate in the gel with the high abundance proteins will be lost. The bands can be cut out by automated methods. Membrane proteins which are typically hydrophobic are hard to access by gel electrophoresis as are alkaline proteins, therefore the subset of proteins that are analysed are depleted of such proteins.

Depletion

In order to prevent high abundance proteins from drowning out low abundance proteins, common high abundance proteins such as human albumin, transferrin, haptoglobin, a-1-antitrypsin, IgG, and IgA or others which have little value as biomarkers or as components of the pathways of interest can be depleted from the protein population. There are a number of depletion kits available including, the ProteoPrep (Sigma) which in some embodiments of the disclosure are applied after protein extraction and preferably before unfolding into linear polypeptide and before analysis.

Equalization of Protein Abundance

As an adjunct or alternative to depletion, the low abundance proteins are enriched at the expense of high abundance proteins. There are a number of enrichment kits available including the ProteoMiner (BioRad). The principle of the approach is the treatment of complex protein samples with a large, highly diverse library of oligopeptides (which are typically attached to a support) whereupon each oligopeptide binds a unique recognition site on a protein. As the capacity of the library is finite, the higher abundance proteins soon saturate the oligopeptides species that they bind to and excess high abundance proteins are washed away. In contrast, the lower abundance proteins do not completely saturate the oligopeptides they bind to or if they do the excess amount of protein that is washed away is small compared to the case for high abundance proteins. The resultant effect is that the concentration of the different abundance classes are equalized to a substantial extent and the dynamic range of proteins in the sample is decreased.

Enrichment of Specific Proteins

Affinity ligands which bind to specific proteins of interest can be provided. For example, the affinity ligands can target proteins implicated in cancer. After their capture, and the removal of non-captured proteins, the captured proteins can be released from the affinity ligands and analysed by the methods of the disclosure. This enrichment can reveal whether a mutant, mis-spliced or truncated version of a protein or a particular low abundance protein is present in a population.

The depletion and enrichment processes can be carried out multiple times to enhance their effect.

In some embodiments of the disclosure the proteins are depleted/enriched/equalized and then subject to sequencing of the polypeptides.

In some embodiments of the disclosure the proteins are depleted/enriched/equalized and then subject to fingerprinting and identification of the polypeptides.

Microfluidic chips containing the principles above, linked with the polypeptide analysis methods of the disclosure are part of the disclosure. Fractionation, depletion, equalization, purification and enrichment can be integrated on chip. Preferably this involves, increasing internal surface area in the chip so that a greater amount of the capture reagents can be loaded onto the chip. The internal surface can be increased by including controlled pore glass or other membranous material, beads or pillars/micro-posts inside the chip.

The advantage of microfluidic approach is integration, ease, increased efficiency and reduction of contamination; depletion methods are multi-step and usually lead to a significant keratin contamination. Also a multitude of polymeric contaminants are released from the plastics used in off-chip methods that can lead to complication of the results. Much of this is avoided when the depletion, equalization or enrichment steps are carried out in the microfluidic device and especially when subsequent analysis steps are integrated in the device. Enrichment, equalization or depletion reagents can be flowed across an army of pillars to which they bind. The protein population is then flowed through and are able to bind to their specific ligands. In case of the depletion approach, what does not bind and flows through, is subject to subsequent steps of the disclosure such as unfolding and the analysis of the features and linear length of the polypeptides. In the case of the equalization and enrichment approach, what does not bind and flows through initially is removed and the proteins that have bound are then eluted and subjected to the subsequent steps of the disclosure such as unfolding and the analysis of the linear length of the polypeptides.

All or some the steps of the disclosure, from sample loading, protein extraction, labeling, unfolding, linearization to detection can be carried out in a lab-on-a-chip device.

Unfolding Proteins

Native proteins comprise tertiary and quaternary three-dimensional structures. Unfolding and refolding of proteins occurs routinely within cells.

In order to practice the methods of this disclosure, native proteins must first be unfolded into linear one-dimensional strings. This can be done in a number of ways by heat, denaturants, and extreme pH. However, Nivala has described the use of an unfoldase, the chaperone protein, ClpX to unfold proteins to their polypeptide form so that they can translocate through a nanopore (Unfoldase-mediated protein translocation through an $\alpha$-hemolysin nanopore. Nivala J, Marks D, Akeson M. Nat Biotechnol. 2013 March; 31(3):247-50). In addition to the approach used by Nivala, it is disclosed herein that chaperone proteins or complexes can be added to a solution containing the proteins to unfold the proteins before they are analysed. This can be done under denaturing conditions so that the polypeptides remain substantially unfolded. Physical methods can be used as an alternative to enzymatic unfolding. This can include the application of heat (e.g., heat to above 75° C.) and/or a number of specific chemicals. The denaturing conditions (e.g., using Urea, Formamide, SDS, GuCl) are compatible with of nanopore and nanochannel measurements depending on the concentration of reagents used. Reducing agents can be used to break disulphide bonds which crosslink different segments of the polypeptide in the protein tertiary structure. Suitable reagents include, TCEP, Dithiothreitol (DTT), and beta-mercaptoethanol (BME). Detergents such as SDS can induce unfolding; the addition of cation (e.g., NaCl) can increase the rate of unfolding. Chaotrophic agents can be used to unfold proteins. Guanidinium chloride is one such effective reagent. Urea (8M at 60° C.) can also be used to unfold proteins.

Molecular Combing, Hydrodynamic Stretching, Electro-Stretching and Molecular Threading The protein can be stretched on a surface by binding the N terminus or C terminus to the surface. The termini can bind a defect on the surface. Preferably the surface is suitably derivatized and the polypeptide binds to a specific chemical group.

Alternatively, one can take advantage of a common set of residues present in a plurality of polypeptides. Many proteins contain a common signal peptide or leader sequence (typically a short 5-30 amino acid length of the N-terminus), which can facilitate transport of the protein. Often the signal peptide comprises a stretch of hydrophobic amino acids that tend to form an alpha-helix. In addition, frequently, signal peptides have a short positively charged stretch of amino acids.

Such leader sequence can be targeted for capture by an antibody recognizing said leader sequence, so that proteins containing the leader sequence can be captured by their leader sequence. Alternatively, in the case of recombinant proteins a leader sequence or tag (e.g., histidine, FLAG-peptide) can be engineered onto the polypeptide; multiple copies of the leader can be included. The leader can then bind to its ligand attached to the surface (e.g., a copper coated surface can bind to histidine). Alternatively, a leader sequence can be conjugated onto the end of all polypeptides by reaction with the N or C terminus. An artificial leader sequence can comprise an unstructured polyanionic sequence such as 65-amino-acid-long glycine/serine tail including 13 interspersed negatively charged aspartate residues. Capture can be on the basis of hydrophobicity (e.g., by contact with alkyl thiols coating a gold surface) or charge (e.g., by contacting positively charged Poly-L-lysine coated surface). Binding to such natural leader sequences can be a way of enriching proteins destined to be secreted. A repertoire of different polypeptide binding reagents can be patterned on a surface so that most all different types of polypeptides can be captured.

As an alternative to a leader sequence one or more biotins can be engineered in vitro or in vivo on to the ends of the polypeptides allowing the polypeptide to be captured on a streptavidin or anti-biotin antibody coated surface.

The surface can be patterned with multiple capture reagents. For example, stripes can be made containing hydrophobic or hydrophilic residues, or residues with negative or positive charges. Polypeptides with different leader sequences can then be immobilized to different locations on the surface.

One of the stretching methods described below can then be applied to the captured polypeptides.

The polypeptide can be combed onto a surface by using a receding mensicus approach. To achieve the receding meniscus a droplet containing the polypeptides may be translated across a surface, or a droplet containing the polypeptides can be allowed to dry on a surface or a surface can be pulled out of a trough containing a solution containing the polypeptides. Molecular combing has been applied to the stretching of the Titin (TTN) polypeptide (Tskhovrebova L; Trinick J Flexibility and extensibility in the titin molecule: Analysis of electron microscope data J MOL BIOL 310 755-771, 2001).

Molecular threading involves dipping a needle into a solution containing the polymer of interest, allowing a single polymer to attach to the tip of the needle and then passing the needle over a surface to deposit and stretch the polymer on the surface. This has been achieved for polynucleotides and can be extended to polypeptides.

Polypeptides can also be stretched by application of an electric field. Preferably one end of the polypeptide is first attached to a surface.

The polypeptides, once attached at one terminus, can be stretched by fluid flow. The polypeptides can then be imaged whilst dangling in the fluid flow. Alternatively, the polypeptides can be allowed to settle on the surface; providing suitable chemical attachment points on the surface can facilitate this. For example, some polypeptides can bind to a negatively charged Mica surface.

As an alternative to stretching polypeptides on the plane of the surface, they can be stretched perpendicular to the surface. This can be done by attaching a bead to one end of the polypeptide and stretching the polypeptide upwards using magnetic tweezers. Confocal microscopy or light sheet microscopy can then, for example, be used to define the locations of labels along the polypeptides.

All the DNA stretching methods that involve the attachment of a DNA end to a surface can be performed on a large number of molecules in parallel. One molecule can be prevented from overlapping with another by tailoring the concentration of polypeptides in the solution from which they are deposited. In the case of molecular threading, a comb-like structure can be used to deposit a plurality of polypeptides in parallel, at predestined separations.

Stretching by Nanoconfinement

As with polynucleotides, polypeptides can be stretched by nanoconfinement, in nanochannels, nanogrooves or nanoslits. The stretching can be facilitated or enhanced by using hydrodynamic flow in combination with nanoconfinement.

Several polypeptides can be stretched, head-to-toe or toe-to-head in a single nanochannel but the dimensions of the nanochannel and the gap in time between entry into the nanochannel will ensure in the majority of cases enough of a gap, that the start of one protein can be differentiated from the end of another. Nevertheless in some embodiments, the start and/or end of the proteins are tagged, preferably with a label that can be differentiated from the labels along the length of the molecule.

Translocating Through a Nanopore

When proteins are unfolded they can be translocated through nanopores (Oukhaled et al Physics Review Letters, 98: 158101). To control the translocation Nivala et al (WO 2013123379) describe controlled unfolding and translocation of proteins through the a-hemolysin (a-HL) pore using the AAA+ unfoldase ClpX. Nature biotechnology, 31: 247 (2013).

ClpX is a component of the ClpXP proteasome-like complex that is responsible for the targeted degradation of numerous protein substrates in *Escherichia coli* and other organisms. ClpX forms a homohexameric ring that uses ATP hydrolysis to unfold and translocate proteins through its central pore and into a proteolytic chamber (ClpP) for degradation. ClpX generates sufficient mechanical force (~20 pN) to denature stable protein folds, and because it translocates along proteins at a rate suitable for primary sequence analysis by nanopore sensors (up to 80 amino acids per second).

Natural or artificial leader sequences at the polypeptide terminus can be deployed to help the polypeptide be attracted to the pore and/or to be threaded through. An ssrA tag can be added for this purpose. This ssrA peptide tag allows ClpX to specifically bind to the C terminus of the protein when it threaded through the pore into the trans compartment Reversing Translocation and Repeating Measurement In order to obtain a better accuracy in determining the characteristics of the polypeptide, measurements can be repeated on an individual polypeptide. This can be done by reversing the direction of translocation, for example, by switching the polarity of the electric field. This can be done while a polypeptide is in the nanopore. Alternatively, immediately after the polypeptide has come all the way through the nanopores the polarity is reversed, providing a very high likelihood that the same polypeptide will be threaded back in and translocated through. During the reverse translocation, measurements can be made. The characteristics of the measurements may differ in the forward and reverse directions, especially if the pore has an asymmetric structure from the trans to the cis side of the membrane.

Threading Polypeptides into Nanopores and Nanochannels

Proteins are heterogeneous, bearing different net charges and different polypeptides have different charges along their length. It is challenging to thread a polypeptide molecule into a nanochannel or nanopores. However the threading can be facilitated by attaching a leader sequence to one or both ends of the polypeptide. When a pore is formed in a lipid bilayer, a cholesterol tag can be used to bring the polypeptide to the lipid bilayer membrane. A polynucleotide sequence, which has a homogenous backbone charge can be added to end of the polypeptide to facilitate its threading into the pore. In addition an array of pillars/microposts or other structures can be placed adjacent to the nanochannel or nanopore/nanogap to guide the polypeptide to the orifice and facilitate threading.

Molecular motors can be used to pull the polypeptide through a pore followed by comparison of the order of lysine and cysteine amino acids to a reference. In some embodiments, it is possible to identify a protein by detecting the order of ~10-25 amino acid residues (e.g., lysine and cysteine amino acid residues) in a single protein.

DNA can be translocated through microchannels, nanochannels and nanopores by pressure driven flow or by electrophoretic flow. Unlike polynucleotides, polypeptides, due to their 20 amino acids, with various charges, have a heterogeneous charge pattern along their length, which makes electrophoretic translocation less straightforward than for the DNA case. Polypeptides can however be translocated using pressure, which acts independently of charge. Nevertheless, much like traditional electrophoresis of proteins, the polypeptides can be contacted with reagents that neutralize charges, i.e. Sodium Dodecyl Sulphate (SDS).

For proteins, sodium dodecyl sulfate (SDS) is an anionic detergent applied to protein sample to denature secondary and non-disulfide linked tertiary structures, leading to linearized polypeptides and imparts a negative charge to the polypeptide.

Heating of a protein or a protein mixture in the presence of SDS can lead to a substantially unfolded state permitting binding of SDS throughout the length of the polypeptide. Once SDS has been bound, the characteristic pI values of the proteins is no longer relevant; the protein takes on a negative charge, and each protein has essentially the same charge to mass ratio.

Proteins that have a greater hydrophobicity such as many membrane proteins, and those that interact with surfactants in their natural milieu, are harder to treat using SDS.

Nevertheless SDS can enable the polypeptide to be treated similarly to a polynucleotide and the stretching and combing and nanopores methods developed for DNA polymers can be applied to and optimized for polypeptides. DTT or other reducing agents can break disulphide bonds, allowing proteins to fully unfold. Such a negatively charged peptide chain would go through a nanopore like a uniformly charged DNA molecule.

One problem is that protein pores can become unstable under certain protein denaturing conditions however, solid-state pores have no such problem. However, the creation of bubbles with addition of SDS makes nanopores measurements somewhat difficult. However, anti-foaming reagents can be added to reduce this problem.

SDS and DTT can be combined, to unfold proteins and to allow them to be stretched on surfaces, in flows, in nano-confinement and be transported through nanopores.

Block Copolymer

One way to practice the disclosure is to fuse the polypeptide with a co-polymer (e.g., polynucleotide) that can be stretched by molecular combing, molecular threading, fluid flow, confinement or by applying an electric field. The stretching of the co-polymer enables the polypeptide to be co-stretched. A polynucleotide sequence of sufficient length to stretch on a surface is covalently linked to the C or N terminus of a polypeptide. In one embodiment, the interaction with the surface is with one of the polypeptide ends and the stretching of the polynucleotide portion of the polymer causes the polypeptide portion to also stretch. Alternatively, both ends of the polypeptide can be linked to polynucleotides. Then the polynucleotide on one side attaches to the surface.

Polypyrole or other conjugated polymers such as polyaniline, poly(ethylenedioxythiophene) can be conjugated to the ends of the polypeptide to provide additional functionality.

Labeling

Protein/polypeptide labeling by chemical means involves the covalent attachment of labels/tags to amino acids using labels conjugated to reactive chemical groups that react with specific amino acid residues. There are a number of functional groups on proteins/polypeptides that are available for labeling for the purposes of this disclosure. This includes the following common types of functional groups: Primary amines ($NH_2$) which exist in lysine side chains and at the N-terminus; Carboxyls (COOH) which are found in aspartic acid, glutamic acid side chains and at the C-terminus; Sulfhydryls (—SH) which are present in the side chain of cysteines; Carbonyls (—CHO) which are created by oxidizing carbohydrate groups in glycoproteins.

Labeling one type of residue is sufficient to fingerprint a protein and to identify it. Optionally more than one type of residue is labeled and preferably each different type of residue is labeled with a distinct tag or label.

In a substantial number of cases the efficiency of labeling may not reach 100% but a sufficient number of labels are achieved per molecule to identify the molecule.

Sypro Ruby and other protein stains can be used to label the polypeptide backbone or certain classes of amino acids such as the basic amino acids in the polypeptide. This helps to visualize the polypeptide. Without a backbone stain the correlation of labeled residues along a traceable line is adequate to visualize the polypeptide. Lysine residues can be labeled by NHS-ester chemistry. Cysteines can be labeled by maleimide chemistry. Histidines can be labeled by binding to metals such as Nickel and Copper. The N- and C-termini can also be labeled. Both cysteine and maleimide chemistry can be used to label a polypeptide, one applied after the other.

Detection

Nanopore-mediated Detection

Solid-state, biological or hybrid nanopores can be used for detection. When the polypeptide enters the pore, a blockade in ionic current is detected. Then when the first label passes the pore a further increase in blockade is detected. When the label has passed the pore the blockade is decreased to the level of the polypeptide alone until the next label is detected. If different labels are used then different degrees or duration of blockade are detected.

An advantage of biological nanopores or pores with some chemical groups attached is that specific functionalities can be engineered into or adjacent to the pore. For example, a molecular motor protein can be attached to facilitate translocation of the polymer. Conjugated polymers can be attached to the biological nanopores (e.g., a DNA nanopore) to provide light emitting or light harvesting capability at the pore. A light emitting capability at the pore leads to on-chip illumination without the need for a separate light source. Similarly, a stain or intercalating dye can be added to a pore comprising DNA origami or nano structure, which emit light at a higher wavelength than that at which they are excited. Similarly, fluorophores, chemically or biologically coated fluorescent nanoparticles such as Quantum Dots (Invitrogen, Carlsbad) can be conjugated to biological pores.

Microscopy-related Detection

Optical imaging and scanning methods can also be used for detection. Typically, the labels should be fluorescent dyes, particles or other structures or light-scattering particles. A CCD or CMOS chip can be used to obtain a wide-field image of an array of polypeptides stretched on a surface or in nanochannels. A particular advantage of detecting polypeptides on surface is that billions of molecules can be stretched on a surface and then detected using fast imaging methods such as the TDI mode. This then is compatible with the dynamic range of proteins that might be encountered. Hence, using such surface-based stretching, even rare or low abundance can be detected with no or little depletion, equalization or enrichment.

Because polypeptides are generally short (e.g., by comparison to a polynucleotide) many useful sites of labeling are likely to be too close together to be resolved by optical microscopy. For this reason it is important to use super-resolution or high spatial resolution detection methods. A label carrying a DNA tag onto which DNA PAINTS can dock allows super-resolution imaging to be conducted. Different tags on labels targeting different amino acids, enables multi-color super-resolution imaging to be obtained.

In scanning optical approaches STED or SNOM microscopy can be used to obtain resolution beyond the diffraction limit of light. A course grained image is first obtained to locate the polypeptides on the surface and then the path of the STED beams can be directed over each of the polypeptides. When the polypeptides are stretched or elongated in nanochannels, then the STED beams can traverse along the path of the nanochannels. The nanochannels can be organized at predetermined locations with respect to their setting into an insert on the microscope or with respect to an easily detectable marker on the substrate.

In some embodiments signal enhancement is achieved by proximity to a metal or by plasmonic effects, including those achieved by using plasmonic structures such as a bow-tie or bulls eye.

Non-optical surface imaging or scanning methods can also be used. This includes the electron microscopies (e.g. Transmission Electron microscopy, Scanning Electron microscopy) and the Scanning probe microscopies (e.g., Scanning Tunneling Microscopy, Atomic Force Microscopy, Scanning Ion Conductance Microscopy). Providing a label with some size larger than the polypeptide width or a shape is sufficient. The electron microscopies benefit from labels containing heavy metals or nanoparticles.

Determining the Pattern of Labels

In one way of practicing the disclosure, the location, distance between and/or order of labels is used to assign an identity to the protein. In another embodiment, a pattern of labels is used to assign the identity. The pattern may not allow one to determine the exact location, distance between or the order of labels. For example, with the resolution available it may not be possible to tell which color label comes first, when the labels are substantially co-localised or a run of the same labels that cannot be resolved may cover a portion of the polypeptide.

The rendition of labels along each polypeptide in the database are blurred to the extent of the optical resolution. So if the optical resolution is 250 nm, any residues that are labeled within a range of 250 nm are blurred into one dot.

Determining the Pattern of a Physico-chemical Property

The polypeptide can be analyzed to determine a pattern of a physicochemical property of the amino acids along its linear length. This property can be the hydrophobicity of an amino acid, the charge on the amino acid etc. The physiochemical property cab be determined by the interaction of the amino acid side chains with a probe. The probe can be an AFM tip, its material composition or coated with a suitable chemical groups or biochemical residues. The probe can also be the residues inside the lumen of a biological nanopore. This can be the native internal nature of the lumen of a wild type pore, for example the Anthrax Toxin Pore has hydrophobic residues in a circular arrangement around its internal diameter [A Phenylalanine Clamp Catalyzes Protein Translocation Through the Anthrax Toxin Pore. Science 29 Jul. 2005: vol. 309 no. 5735 777-781]. The very hydrophobic amino acids comprise: valine, isoleucine, leucine, methionine, phenylalanine, tryptophan, and cysteine.

The pore can also be engineered to present a specific physicochemical property. For example, a cyclodextrin (or its derivatives) can be inserted into a nanopore to make the interior of the pore hydrophobic. When hydrophobic residues interact with the hydrophobic side chains, in an aqueous environment, the translocation of the polypeptide through the pore can show patterns of stalling. This leads to a characteristic pattern for a given protein, as each protein has a somewhat unique pattern of hydrophobic residues.

Other intrinsic features of the polypeptide that can be analysed include its electrostatic properties, adhesive properties, local folded state (see below), backbone flexibility (e.g., increased flexibility shows up as increased noise in a nanopores trace), elasticity, mechanical stability, stickiness, fluorescence (see below), absorbance, and binding affinity to ligands.

A number of physico-chemical properties of the polypeptides can be determined by conducting Force-Distance curves using an Atomic Force Microscope (AFM). The AFM tip approaches and withdraws from the sample on a pixel by pixel basis and measures interaction forces of the tip with the polypeptide. The pixel sizes can be below 1 nm and the positional accuracy can be 0.2 nm. AFMs are capable of performing large arrays of Force-Distance curves and means for this is integrated into the software available form leading AFM vendors (e.g., Bruker). An array of Force-Distance curves enables multi-parametric imaging which includes: topographic, deformation, energy dissipation, elasticity, adhesion etc. information. Different regions of the polypeptide, comprising one or more amino acids, will give different responses in the force curves. These can be displayed as a heat map across the polypeptide and each polypeptide will have a unique heat map for at least one of the physico-chemical properties determined. The unique map of the physico-chemical property can be compared to the database of polypeptide containing experimentally derived or calculated patterns to provide likelihoods for matches between the analysed polypeptide and the polypeptides in the database. A combination of maps of different physico-chemical properties can be used to make the match. The AFM tip can be composed of different material and can be coated with material (e.g., an antibody, a thiol group) that will give a particular character to the physico-chemical measurement obtained. For example, a thiol coated tip will interact with cysteine residues to give an increased adhesion.

It is not necessary to know the basis of the physico-chemical phenomena being detected.

Determining the Pattern of Local Secondary Structure

Under particular denaturation conditions some types of local secondary structure will remain in a polypeptide, and can be used as a way of identifying a particular protein, without or in addition to labeling specific residues. Such local secondary structure can be detected by scanning probe microscopies or nanopores detection, for example. The experimentally derived database will, in this case, comprise proteins substantially treated and tested under the same conditions as the polypeptide being tested.

Determining the Pattern of Intrinsic Fluorescence

Three amino acid residues, tryptophan tyrosine and phenylalanine are intrinsically fluorescent. However, they are neither bright nor photostable enough for standard single-molecule measurements. However, their fluorescence can be enhanced by proximity to a metal. Polypeptides are translocated through a nanopores or nanochannel designed with integrated metallic structures to enhance fluorescence; the enhanced fluorescence occurs at a detection station such as a nanopore, on a surface or in a nanochannel/nanoslit.

Determining the Location of Labels or Distance Between two or more Labels

There are two ways that the location of labels can be determined. One is by precise coordinates of each label in relation to the start and end of the detectable length of the polypeptide. The length and coordinates of the label can be determined by making physical measurements of distance. For example, this can be done by using a calibrated optical microscope or AFM. If the ends of the polypeptide are not precisely determined, for example if the ends have curled up, are not fully stretched or remain globular, then the distance between labels can be determined. The same principles can be applied to the detection of the location of or distance between particularly physico-chemical properties.

Alternatively the length can be determined by using time of translocation through a nanopore as a proxy. For example, when the polypeptide enters the nanopore an increase in blockade in ionic current can be detected. When the polypeptide leaves the pore a decrease in blockage is detected. How the time of translocation relates to distances or lengths can be calibrated by using one or more standards. When a label on the polypeptide passes the pore, a characteristic change in the ion blockade can be detected, e.g., a further increase in blockade is detected while the part of the polypeptide bearing the label is in the nanopore. If the label stalls or slows down the translocation of the polypeptide, the blockade event is longer lived. The temporal occurrence of the increased blockade and its duration in relation to the blockade associated with the translocation of the polypeptide is recorded. If there are multiple labels multiple blockades will be detected. This same principle of changes in extent and duration of ion blockade is applied when physico-chemical properties rather than labels are detected. A pattern of ionic flux changes (e.g., blockades) are determined for the length of the polypeptide and can be examined to reveal the location of labels in relation to the start and end of the polypeptide. If the blockade corresponding to the ends of the polypeptide are not recorded or not used, the time between consecutive blockades due to the labels can be detected.

Determining the Relative Order of two or more Labels

When two or more labels are used the location of or distance between labels need not be determined, just determining the relative order of the different labels is sufficient to define a specific signature for a particular polypeptide in order to determine its identity.

Comparison to a Database

An identity can be assigned to a protein, without necessarily carrying out a comparison to a database. In some case it is sufficient to say that a given protein is distinct from another protein based on its pattern. However in other cases a comparison is made against a database to determine if a match to the protein exists in the database and if it does, what protein in the database it corresponds to. If the pattern corresponds to the expected pattern of a protein in the database (the primary sequence of such proteins should be substantially known) then it is reasonable to assume that the experimentally derived pattern is for the same protein (or at least a closely related protein) as that matched in the database. This comparison can be made in a number of ways (or a combination of ways). The first is just by pattern matching. The following three are by obtaining specific types of data. The second is by comparing the order of labels on the polypeptide to the expected order of labels of candidate proteins in the database. The third is by using the reasonably precise coordinates of the label on the polypeptide and the fourth is to use the reasonably precisely determined distance between each of the labels on the polypeptide to compare against a database of proteins containing such data. The experimentally derived data is normalized to take into account the physical rendering of the polypeptide. For example the extent of unfolding or stretching will determine the distance between labels or the rate of translocation of the polypeptide will determine the distance between labels (using time as a proxy for distance). This normalization can be done against a spiked-in known polypeptide (or other polymer) with known distances between labels. As an alternative to such normalization, a number of different stretching factors can be computationally applied to the experimentally derived patterns or data and then a comparison at each stretching factor can be done against the database. A match to the database at a particular arbitrarily assigned stretching (even if the actual stretching factor is not determined) can be sufficient to make a determination of the identity of the protein. To allow for splice isoforms and mutant proteins, the complete pattern may not match the database but if a substantial part matches, especially over a contiguous stretch, then the identity of the protein is assigned to the match with the caveat that the protein may be an isoform or a mutant. In some cases the protein will be a fusion protein. In this case, part of the experimentally derived data or pattern for a single polypeptide will match one protein in the database and another part of the experimentally derived data or pattern will match another protein (or no protein) in the database. Usually the match to each of the proteins in the database will only be over part of the length of the protein in the database. In some cases the pattern or data from a polypeptide will be partial because the protein may be truncated or it may have broken during handling.

In most cases, the experimentally derived pattern is compared to an in silico generated pattern by using parallel computing. For example, the analysis can be run using a graphics card (GPU) on a desktop or laptop computer. Here the matching problem can be broken into segments and each segment is run on a different core of the GPU. One way to do this is to assign an equal fraction of the database to each of the cores and then to run the comparison with the experimentally derived data or pattern in each of the cores, in parallel.

The database can be constructed by gathering the sequence data of a complete or partial set of proteins and performing computational analysis on each protein to access its length, the location of residues along its length and entering it into a column linked to the protein name or accession number.

As an alternative, the database comprises or in addition comprises, entries derived from experimental data/patterns rather than expected data or predicted patterns. These entries are derived from the prior analysis of individual proteins, which have been tested in a purified or substantially purified form. For example, a recombinant protein is expressed and purified and then treated according to the experimental embodiments of the disclosure and a pattern of labels or a data comprising location of labels, distance between labels or order of labels of different varieties are obtained and deposited in the database. A polypeptide under analysis is then compared to the obtained database comprising of experimentally derived data and/or in silico calculated data. If a particular polypeptide is not found in the database, its pattern or data can be added to the database. Then further occurrences of the polypeptide can be matched to the database.

Read Depth and Throughput

In order to access the least abundant or rarest proteins, the number of proteins that must be analysed is huge. A large array of nanopores (e.g., ~1 million) or fast microscopy based approaches are needed. Also to achieve sufficient throughput with nanopore methods, as fast a speed of translocation that can borne by the detection system should be used. This necessitates the avoidance of motor proteins and chaperonins such as ClpX and prefers fast translocation using electrophoretic forces for example, at a speed that does not provide resolution of every amino acid. Not achieving resolution of every amino acid is compatible with detection of the occurrences of cysteine and/or lysines, for example the occurrence of 1 out of the 20 or 2 out of the 20 different amino acids will be less frequent and require lower resolution to be detected.

With optical approaches, Time-Delay Integration (TDI) based imaging is preferred. Super-resolution optical, scanning probe or electron microscopies allow a greater density of molecules to be imaged per area. However, to achieve high throughput super-resolution, optical imaging methods those that require the imaging of a field of view over multiple frames should be preferably avoided. Methods that utilize the previously characterized point spread function of known fluorescent labels to calculate an image in super-resolution are preferred. Of the non-optical approaches electron microscopy is preferred because an image of a large number of molecules can be obtained using a 2-D detector such as a CCD camera. It is preferred that time-delayed integration CCD imaging is used where stage movements are coupled with chip read-off. High-speed SPM can also be used.

One advantage of mapping specific residues, is that there is a massive speed-up compared to when all residues have to be detected (and discriminated). In most cases only a pattern or the order of labels or approximate location or distance between residues is needed. In these cases objective magnification as low as 40× and 20× can be used (preferable with high numerical aperture optics, such as Zeiss 20× 0.8 NA or Nikon 20× 0.75 NA). When this is coupled with TDI imaging with a large chip a very large number of molecules can be imaged in a short space of time. The limit to the speed can become the rate at which the data is transferred off the CCD chip to the computer. This data transfer rate will improve over time.

Alternative Embodiments

The methods described above can be extended beyond polypeptides. In some embodiments a polynucleotide passes a fluorophore, whose fluorescence emission is sensitive to its physical environment and different bases, base sequence motifs, 2 mers, 3 mer, 4 mers, 5 mers, 6 mers or labels thereon elicit different fluorescent responses such as attenuation of the signal. In some embodiments, the label on the residue is a quencher and quenches the signal of the label at the detection station. In related embodiment one or more contiguous bases directly elicit some change in an optical property at the detection station. In some embodiments the label on the one or more base is a FRET acceptor and the label on the detection station is a FRET Donor or vice versa.

Computer Implementations

It should be appreciated that methods disclosed herein may be implemented in any of numerous ways. For example, certain embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a smart phone, tablet, or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools (e.g., MATLAB), and also may be compiled as executable machine language code or intermediate code that is executed on a framework or virtual machine.

In this respect, aspects of the disclosure may be embodied as a computer readable medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer storage medium) encoded with information (e.g., protein fingerprint or sequence information) and/or one or more programs that, when executed on one or more computers or other processors, perform methods that implement the various embodiments of the disclosure discussed above. The computer readable medium or media can be transportable, such that the program or programs stored thereon can be loaded onto one or more different computers or other processors to implement various aspects of the present disclosure as discussed above. As used herein, the term "non-transitory computer-readable storage medium" encompasses only a computer-readable medium that can be considered to be a manufacture (e.g., article of manufacture) or a machine.

The terms "program" or "software" are used herein in a generic sense to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

As used herein, the term "database" generally refers to a collection of data arranged for ease and speed of search and retrieval. Further, a database typically comprises logical and physical data structures. Those skilled in the art will recognize methods described herein may be used with any type of database including a relational database, an object-relational database and an XML-based database, where XML stands for "eXtensible-Markup-Language". For example, protein fingerprint or sequence information may be stored in and retrieved from a database.

Computer-executable instructions may be in many forms, such as program modules, executed by one or more computers or other devices. Generally, program modules include routines, programs, objects, components, data structures, etc. that perform particular tasks (e.g., tasks relating to Feedback control) or implement particular abstract data types. Typically the functionality of the program modules may be combined or distributed as desired in various embodiments.

EXAMPLES

An example workflow for protein fingerprinting and analysis is provided in FIG. 1. Supporting details and experimental methods are provided below and elsewhere herein.

Extraction

Cytoplasmic proteins from PC12 cells, can be extracted using 40-50% of the CelLytic-M solution and is almost complete within 2 minutes. 100% CelLytic-M allows all cellular proteins to be extracted. The reaction can be performed on individual cells trapped in wells or regions of a microfluidic device. Serum can be extracted from blood using standard methods. The cells can be spun down and this can be followed by the lysis methods described herein.

Single Cell

Spreading single cells into well array. With non-lipid membrane containing nanopore systems, the cells can be lysed using detergents. This the protein contents of the cell can spill out. In order to encourage transport of proteins rather than nucleic acids, nucleases can be added so that DNA and RNA are degraded, leaving only polypeptides being the predominant polymer to transit through the pores. Nuclear proteins can be analysed by increasing the detergent concentration, e.g., to 100%.

Unfolding

Proteins may optionally be briefly heated to near boiling in the presence of a reducing agent, such as dithiothreitol (DTT) or 2-mercaptoethanol (beta-mercaptoethanol/BME), which further denatures the proteins by reducing disulfide linkages, thus overcoming some forms of tertiary protein folding, and breaking up quaternary protein structure (oligomeric subunits).

The following is a table shows non-limiting example of protein bioconjugation methods (related reagents are commercially available, e.g., from Life Technologies (Carlsbad)):

Primary amines (—NH2): This group exists at the N-terminus of each polypeptide chain (called the alpha-amine) and in the side chain of lysine (Lys, K) residues (called the epsilon-amine). Because of its positive charge at physiologic conditions, primary amines are usually outward-facing (e.g., on the outer surface) of proteins; thus, they are usually accessible for conjugation without denaturing protein structure.

Carboxyls (—COOH): This group exists at the C-terminus of each polypeptide chain and in the side chains of aspartic acid (Asp, D) and glutamic acid (Glu, E). Like primary amines, carboxyls are usually on the surface of protein structure.

Sulfhydryls (—SH): This group exists in the side chain of cysteine (Cys, C). Often, as part of a protein's secondary or tertiary structure, cysteines are joined together between their side chains via disulfide bonds (—S—S—). These must be reduced to sulfhydryls to make them available for crosslinking by most types of reactive groups.

Carbonyls (—CHO): Ketone or aldehyde groups can be created in glycoproteins by oxidizing the polysaccharide post-translational modifications (glycosylation) with sodium meta-periodate.

The following reference is incorporated by example, and is instructive on a number of methods for labeling specific amino acids or subsets thereof: Angew Chem Int Ed Engl. 2009; 48(38): 6974-6998.

The following is one of the protocols for labeling amines (i.e. lysine) using Cy3 NHS Ester, Cy5 NHS ester, Alkyne STp ester, Azide NHS ester form Lumiprobe LLC (lumiprobe.com). The following protocol is according the Lumiprobe recommendation.

1. Determine volume of reaction mixture. The labeling can be performed on any scale from nanomols to dozens of grams. When the scale is low, use minimal volume (10-20 uL). Higher concentrations (1-10 mg of amino-biomolecule per mL of mixture) is optimal.

2. Dissolve NHS ester in ⅒ reaction volume of DMF or DMSO. Amine-free DMF is preferred solvent. After the reaction, NHS ester can be stored in solution for 1-2 months at 20° C.

3. Dissolve biomolecule in 9/10 reaction volume of buffer with pH 8.3-8.5. 0.1 M Sodium bicarbonate solution has appropriate pH. Other alternatives are 0.1 M Tris buffer (although Tris has amino group, it is hindered and does not react with NHS esters), or 0.1 M phosphate buffer. Note pH is most important thing. When doing large-scale labeling (hundreds of milligrams of NHS ester), note that the mixture tends to acidify with time because of hydrolysis of NHS ester. Monitor pH, or use more concentrated buffer then.

4. Add NHS ester solution to the solution of biomolecule, and vortex well. Keep on ice overnight, or at room temperature during at least 4 hours.

6. Purify the conjugate using appropriate method: gel-filtration for macromolecules is most universal. Precipitation and chromatography is another alternative. Organic impurities (such as N-hydroxysuccinimide, NHS ester, acid produced by hydrolysis) are almost always easily separated.

For higher efficiency labelling the ratio of active ester to proteins can be increased to as high is tolerated. A range of denaturants including urea can be tested for compatibility with subsequent steps (specific concentrations are given below for labeling of cysteines).

Cysteines and Lysines can be modified quire routinely using a number of available kits and protocols. But other amino acids can also be specifically labeled. For example, it has been shown that tyrosine can be modified through specific electrophilic aromatic substitutions (EAS) reactions (Stephanopoulos, N.; Francis, M. B. (2011). "Choosing an effective protein bioconjugation strategy". Nature Chemical Biology 7 (12): 876-884).

Labeling of Luciferase Protein as a Model

To exemplify the approach we chose to incorporate biotinylated lysine into combined in vitro transcription/translation (TNT kit, Promega) of a plasmid containing the Luciferin gene. The biotin was incorporated by use of Transcend biotin lysyl-tRNA (Promega) as part of the translation reaction. The following reaction protocol was used:

TNT Quick master mix, 40 ul
Methionine, 1 ul
Plasmid DNA template (control), 2 ul
Transcend biotin lysyl-tRNA, 2 ul
Nuclease Free water, 5 ul
Total 50 ul
30 degrees C. for 90 minute Following the reaction the biotin was reacted with streptavidin and purified using the Slide-O-Lyser (Invitrogen).

The labeled Luciferin polypeptide was now ready for analysis.

Labeling of Titin Protein as a Model

The highly reactive Cys (SH groups) residues in Titin can be labeled using iodoacetamide (see Journal of Muscle Research and Cell Motility 23: 499-511, 2002).

Purification

After labeling the proteins can be purified by one of a number of available methods. The following is one type of kit that is available (Life Technologies) to separate protein from unlabeled reactants.

Slide-A-Lyzer™ MINI Dialysis Device, 2K MWCO, 0.1 mL, 20K MWCO, 0.1 mL (Invitrogen)

Tailing

Oligo- or poly-peptide (e.g., Polyanion) tails can be grafted onto the N- or C-terminals of proteins. There are a number of chemical approaches for making such modifications. One example which is general to N-terminal residues, is their conversion into 2-oxoacyl groups by reaction of the α-amino group with glyoxylate, a reaction catalysed by a bivalent cation, e.g., Cu2+, and a base, e.g., acetate.

An example of C-termini modification is the native chemical ligation (NCL), which is the coupling between a C-terminal thioester and a N-terminal cysteine.

Hetero-bifunctional crosslinkers or PEG can be used to make attachments to N-C-terminal ends.

This allows for example, the appending of a 65-amino-acid-long glycine/serine tail including 13 interspersed negatively charged aspartate residues. This unstructured polyanion was designed by Nivala et al to promote capture and retention of the polypeptide end in the electric field across the nanopore. The appended polyanion can be capped at its C terminus with the ssrA tag, an 11-amino-acid ClpX-targeting motif. The ssrA tag san also be added directly to the polypeptide, without the intervening glycine/serine tail.

Oligonucleotides or polynucleotides can be grafted onto the N- or C-termini of polypeptides in the same way.

Stretching Polypeptides by Molecular Combing

Polypeptides can be deposited onto a surface suitable for AFM imaging, in a chain-like substantially non-globular state, with the use of reagents that render or maintain the chain relatively free of higher order structures and prevent aggregation (e.g., Urea). Polypeptides can be extended by molecular combing using a receding meniscus. This can be done in one of two ways: (a) by moving a droplet containing the polypeptides over a suitable surface, (b) dipping and pulling out a substrate from a reservoir containing the polypeptides, (c) drying of a droplet on a surface.

The proteins (e.g., Titin) are diluted with PBS solution (10 mM K-phosphate pH 7.4, 140 mM NaCl, 0.02% NaN3) containing 50% glycerol to an approximate final protein concentration of 20 μg/ml. In typical experiments urea is added to a final concentration of 1 M to reduce protein aggregation. Optionally 1M Guanidinium Chloride is added to minimize globular folding within the polypeptide. 20 μl sample is applied to freshly cleaved mica and immediately spun in a rotor with 13,000 RPM for 10 s. The rotor, a flat round anodized aluminum block, holds the mica sheet at a radius of 5 cm from the rotation axis of a tabletop centrifuge. Following spinning, but before the complete drying of the residual liquid layer, the mica surface is extensively washed with distilled H2O and dried with clean N2 gas. Optionally the specimen is dried further under ambient conditions prior to AFM imaging. Optionally the sample is covered with PBS solution immediately after the centrifugation step.

DNA Facilitated Molecular Combing.

DNA was grafted onto the N terminal of the protein (see above). The Protein was attached to the surface via its N terminus and its stretching was facilitated by the DNA part being stretched by a receding meniscus and being deposited on the surface. YOYO-1 of Sybr Gold staining of the DNA facilitated locating of the polypeptide-DNA hybrids, allowing interrogation of the polypeptide portion to occur by super-resolution DNA PAINT imaging and other methods of this invention.

AFM Imaging on Mica

The purified protein (s) (Luciferin, Titin, or a proteomic mixture) was diluted with PBS solution (10 mM K-phosphate pH 7.4, 140 mM NaCl, 0.02% NaN3) containing 50% glycerol to an approximate final concentration of 20 µg/ml. Urea and Guanidinium Chloride were each added to a final concentration of 1 M. 20 µl sample was applied to freshly cleaved mica (attached to a small Puck) and immediately spun by taping to the flat section of a rotor with 13,000 RPM for 10 s. Following spinning, the mica was allowed to dry.

The mica was attached via the puck to the magnetic loading surface of a Multimode Scanning Probe Microscope (Bruker, Germany). A silicon nitride, SNL-10 AFM cantilever was attached to the fluid cell of the AFM and loaded onto the AFM head. Buffer was added between the cantilever and mica surface, through one of the inlets of the fluid cell and the cantilever was brought towards the surface until the fluid formed a visible meniscus. The instrument software was opened and tapping mode selected. The laser was focused on the back of the cantilever. The cantilever was tuned. After further approach to towards the surface using the toggle on the multimode AFM, software approach was commenced. Upon tip engagement to the surface, the set point voltage was optimized to obtain an image of sufficient quality to see labeled polypeptides on the surface.

Optical Imaging on Mica

A TNT reaction of Luciferin was conducted but instead of incorporating biotin, a fluorescent dye was incorporated at the lysine residues. The protein was deposited on Mica as described above. The Mica was sandwiched with a cover glass with imaging buffer, containing anti-fade components (e.g., SlowFade, Invitrogen). The cover glass was placed on an upright epifluorescence microscope or inverted and placed on an inverted microscope. Focus was obtained through the cover glass onto the Mica surface, using lamp illumination with appropriate filter for fluorescein or 488 nm laser illumination.

Super-resolution Imaging on Cover Glass

Polypeptides were stretched on a surface using molecular combining. A TNT reaction was conducted to incorporate biotin, and a biotinylated oligonucleotide comprising docking sequence for DNA PAINT oligs was attached via streptavidin. Imaging of lysine locations, closer than the diffraction limit was done by adding complementary PAINT oligos and a super-resolution image was constructed using the DNA PAINT image reconstruction methods (Jungmann. NanoLetters, 2010, 10: 4756-4761.

Molecular Motor Assisted Nanopore Measurements

All experiments were performed in buffer containing 200 mM KCl, 5 mM MgCl2, 10% glycerol and 25 mM HEPES-KOH pH 7.6. Setup of the nanopore device and insertion of an α-Hemolysin (HL) nanopore into a lipid bilayer was as follows a single α-HL nanopore was inserted into a lipid bilayer that separates two wells that each contained 100 µl of buffer. A constant 180 mV potential was applied across the bilayer and ionic current was measured through the nanopore between Ag/AgCl electrodes in series with an integrating patch clamp amplifier (Axopatch 200B, Molecular Devices) in voltage clamp mode. Insertion of a single nanopores led to a current of approximately 65 pA. Data were recorded using an analog-to-digital converter (Digidata 1440A, Molecular Devices) at 100 kHz bandwidth in whole-cell configuration then filtered at 2 kHz using an analog low-pass Bessel filter. Experimental conditions were prepared by the daily preparation of Buffer/ATP 5 mM and Buffer/ATP 4 mM. ClpX was diluted 1:10 in Buffer/ATP 5 mM for a final concentration of 30-100 nM ClpX6 in 4.5 mM ATP final. Then ClpX and ATP were added to the trans compartment.

ClpX solution was used to fill the entire system before isolation of a single α-HL nanopore. Upon insertion, the cis well was perfused with ~6 mL Buffer/ATP 4 mM. Experiments were conducted at 30° C. with 1-2 µM substrate added to the cis well. Similar experiments were conducted using ClpXP in place of ClpX.

When a signal (ssrA) tag had been added to the protein(s) ClpX hexamers in the trans bath (on the opposite side of the bilayer from protein substrate addition) are able to bind to the ssrA tag once it entered the trans compartment. Translocation is facilitated in an ATP-dependent manner.

Analysis of the current traces was used to determine blockade magnitude duration and frequencies.

Nanopore Measurements Without Molecular Motor

A nanopores set up as above was used with the following modifications. The α-HL nanopores replaced with an aerolysin nanopore, a high salt buffer (1 M KCl and 1 M Gdm-HCl, 5 mM HEPES, pH 7.4). Data were filtered at 10 kHz and acquired at 4 µs intervals with the DigiData 1322A digitizer coupled to Clamplex software (Axon Instruments, USA).

In addition, labeled Bovine Serum Albumin (BSA) was analysed according to Protein Pept Lett. 2014 March; 21(3): 256-265. To denature BSA, 1.4 mg SDS (3.9 mM) with 2 mM DTT was added to the stock BSA (1 mg BSA in 1 ml) solution. This mixture was heated at 45° for 5 minutes, then immediately cooled down in a water bath at room temperature. This BSA treated with SDS+DTT and heated at 45°, 60° or 90° and added to the cis chamber. In this experiment the center part of a solid-state nanopore device is a single nanopore fabricated in an insulating membrane (silicon nitride) which separates two PDMS chambers filled with salt solution: protein samples is added to the cis chamber, and protein molecules move into the trans chamber after translocating through the nanopore. A pair of silver chloride electrodes is implanted in the chambers. The electrodes are used to apply a constant voltage across the membrane and to measure the ionic current through the nanopore. The cis chamber is optionally electrically grounded and the trans is positively biased. The nanopores in silicon are fabricated by a Focused Ion Beam (FIB) or by a combination of FIB and low energy noble gas ion beam. The nanopores are typically 10-30 nm in thickness, preferably around 16 nm, and 2-25 nm in diameter. The electrolyte solution contained 1M KCl with 10 mM Tris and 1 mM EDTA at pH 7. A 1 mg/ml stock solution of BSA protein (Sigma-Aldrich) was dissolved to make (~15 µM) in ~150 mM KCl TE buffer. The trans chamber was positively biased to drive the negatively charged BSA (pH 7) to pass through the nanopore. The ionic current signal was recorded using an Axopatch 200B (Molecular Devices) in event driven and voltage-clamp mode. The low pass Bessel filter in the Axopatch 200B was set to 10 kHz or 100 kHz.

Working Example of Cell to Analysis

Cells from NIH 3T3 adherent cell line were harvested by trypsinization, diluted with nine volumes of lysis buffer (7 M urea, 2M thiourea, 10 mM Tris, 4% CHAPS, 5 mM magnesium acetate pH to 8.0) incubated on ice for 30 min, and sonicated on wet ice using 25 s pulses at 5-6 microns amplitude with 1 min cooling period until clear. Centrifuged at +4° C. at 12000×g for 10 min. Pellet discarded and protein concentration of supernatant determined by using an aliquot. Lysines in the proteomic sample (50 µg) were then labelled with 0.4-400 nmol of CyDye DIGE Fluor Cy2, Cy3 or Cy5 dye (GE Healthcare) (ideally optimized in this range). Following published results (Electrophoresis 2003, 24, 2348-2358), Cysteines were labeled by taking 25 mM proteomic sample, reduced with variable amounts of TCEP in 8M urea, 50 mM Tris-HCl (pH 7.5 or pH 8.0) and then alkylated with fluorescent thiol-reactive dye (BODIPY TMR cadaverine IA and BODIPY Fl C 1-I) for 1.5-2 h. The reaction was typically quenched by the addition of 150-fold excess of 2-mercaptoethanol for 30 min. In some cases, labeled proteins were purified from free dye using a PD-10 column. In general the dye concentration must be equal to or greater than TCEP concentration. A typical ratio of 9:1 for TCEP over thiol and, 1.125:1 of dye over TCEP (or 10:1 of dye over thiol) was effective in reducing and labeling proteins that had multiple disulfide bonds in a 90 min reaction time, complete labeling was achieved at a dye:thiol ratio of 10:1 and a TCEP:thiol ratio of 9:1 (but can be increased to 75:1) efficient labeling takes place even in the presence of 8M urea; this kept the polypeptides in an unfolded state. The labeled proteins were then optionally purified or directly analysed by nanopores analysis, with post-processing filters applied to remove noise from unpurified reaction components such as unreacted dyes.

Single cells are processed in the same way by conducting lysis in a microwell (10-30 pL volume) (after Sasuga et al. Anl. Chem. 2008, 80, 9141-9149) and labeling directly (without concentration being determined or cell debris being removed). In some experiments these wells contain nanopores systems as described elsewhere in this document, buffer and reagents and appropriately localized electrodes, for nanopores analysis of the sites of labelling on individual proteins to be conducted. Alternatively, the protocol is carried out in a microfluidic device in which individuals cells are trapped and the contents released into a microchannel or chamber, using the above lysis buffer, and collecting the proteomic mixture in a region of the chip where the labeling reagents were added. The proteomic mixture is then fed into a nanopores measuring system or into nanochannels or attached to a surface within the chip and stretched, allowing optical imaging of the location of the labels along the polypeptides, to be conducted.

Finding a Match Between Experimental and in Silico Data

The coordinates of the labels along each polypeptide were determined using image processing tools (ImageJ) and stored in computer memory. The experimentally derived coordinates from the model proteins were then computationally compared to coordinates of the protein stored in computer memory. In the case when data from a mixture of proteins of unknown composition was obtained experimentally, the labeling pattern on each polypeptide as compared to a the expected pattern of a list of proteins in the database (e.g., using Amazon (EC2/S3) and Digital Ocean) to find the best match.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should be appreciated that features of separately-recited embodiments can be combined in any desired combination which may be apparent to those skilled in the art.

What is claimed is:

1. A method for analysing a protein, the method comprising:
   i. unfolding a protein into a polypeptide;
   ii. tagging lysine residues on the polypeptide with biotin;
   iii. stretching the polypeptide on a surface rendering the polypeptide such that the location, distance between and/or order of the biotinylated lysine residues along the polypeptide can be determined;
   iv. conjugating the stretched polypeptide with a first oligonucleotide using streptavidin; and
   v. contacting the stretched polypeptide conjugated to the first oligonucleotide with a second fluorescent-labelled oligonucleotide complementary to the first oligionucleotides and detecting bound fluorescent-labelled oligonucleotides.

2. The method of claim 1, wherein step iii is performed before step ii.

3. A method according to claim 1 where the unfolding is conducted via a mechanical, chemical or enzymatic method or a combination thereof.

4. A method according to claim 1 where the unfolding is facilitated by a molecular motor comprising ClpX or ClpXP.

5. A method according to claim 1, wherein the location, distance between and/or order of fluorescent-labelled lysine residues along each polypeptide are compared to an in silico database of location, distance between and/or order of amino acid residues along polypeptides with a known amino acid sequence.

6. A method according to claim 5, wherein a substantial match to an entry in the in silico database reveals the identity of the protein.

7. A method according to claim 5, comprising comparing data from each individual polypeptide to a protein database.

8. A method according to claim 1, wherein the surface is present in a nanochannel, nanogroove or nanoslit.

9. A method according to claim 1, wherein the fluorescent-labelled oligonucleotides are detected using DNA Points Accumulation for Imaging in Nanoscale Topography methodology.

10. A method according to claim 9, wherein a super-resolution image is constructed from the DNA Points Accumulation for Imaging in Nanoscale Topography.

11. A method according to claim 1, wherein a nucleic acid is attached to the N- or C-terminus of the protein so as to enable stretching the polypeptide.

12. The method of claim 1, wherein the protein is in a mixture of different proteins.

13. The method of claim 12, wherein the mixture of different proteins is a proteome.

14. The method of claim 13, wherein the proteome is from a single cell.

15. The method of claim 12, wherein at least one type of protein is depleted from the mixture of different proteins prior to step i.

16. A method for analysing a protein, the method comprising:
   i. unfolding the protein into a polypeptide;
   ii. tagging selected residues on the polypeptide with labels;
   iii. stretching the polypeptide on a surface such that the location, distance between and/or order of the labels can be resolved; and
   iv. determining the location of labels along the polypeptide using a super-resolution beyond a diffraction limit method.

* * * * *